(12) United States Patent
Myrick

(10) Patent No.: US 6,929,914 B2
(45) Date of Patent: Aug. 16, 2005

(54) METHOD FOR ACCELERATED GENOME WALKING AND DNA FINGERPRINTING

(75) Inventor: Kyl V. Myrick, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 382 days.

(21) Appl. No.: 10/103,200

(22) Filed: Mar. 21, 2002

(65) Prior Publication Data

US 2003/0059795 A1 Mar. 27, 2003

Related U.S. Application Data

(60) Provisional application No. 60/277,690, filed on Mar. 21, 2001.

(51) Int. Cl.[7] ................................................. C12Q 1/68
(52) U.S. Cl. ........................................................ 435/6
(58) Field of Search .......................... 435/6, 91.1, 91.2; 536/23.1, 24.3

(56) References Cited

PUBLICATIONS

Megonigal et al. Panhandle PCR for cDNA: A rapid method for isolation of MLL fusion transcripts involving unknown partner genes. Aug. 15, 2000. PNAS. 97:9597–9602.*
Barnes, Wayne. PCR amplification of up to 35–kb DNA with high fidelity and high yield from lambda bacteriophage templates. 1994. PNAS. 91:2216–2220.*
Kwong–Kwok, Wong et al. Use of tagged random hexamer amplification (TRHA) to clone and sequence minute quantities of DNA–application to a 180 kb plasmid isolated from Sphingomonas F199. Nucleic Acids Research. 24:3778–3783.*
Bedwell, Joanne et al. Identification of substrains of BCG vaccine using multiplex PCR. 2001. Vaccine. 19:2146–2151.*
Huang et al., Recovery of DNA sequences flanking P.element insertions: inverse PCR and plasmid rescue, *Drosophila Protocols*, pp. 429–437, 2000.
Jones et al., Sequence specific generation of a DNA panhandle permits PCR amplification of unknown flanking DNA, *Nucleic Acids Res.*, 20:595–600, 1992.

Liu et al., Thermal asymmetric interlaced PCR: automatable amplification and sequencing of insert and fragments from P1 and YAC clones for chromosome walking, *Genomics* 25:674–681, 1995.
Megonigal et al., Panhandle PCR for cDNA: a rapid method for isolation of MLL fusion transcripts involving unknown partner genes, *Proc. Natl. Acad. Sci.* 97:9597–9602 (2000).
Mueller et al., *In Vivo* footprinting of a muscle specific enhancer by litigation mediated PCR, *Science* 246:780–786, 1989.
Ochman et al., Genetic applications of an inverse polymerase chain reaction, *Genetics* 120:621–623, 1988.
Puskas et al., Restricted PCR: amplification of an individual sequence flanked by a highly repetitive element from total human DNA, *Nucleic Acids Res.*, 22:3251–3252, 1994.
Riley et al., A novel, rapid method for the isolation of terminal sequences from yeast artificial chromosome (YAC) clones, *Nucleic Acids Res.*, 18:2887–2890, 1990.
Sanger et al., DNA sequencing with chain–terminating inhibitors, *Proc. Natl. Acad. Sci.*, 74:5463–5467, 1977.
Schmidt et al, Detection and direct genomic sequencing of multiple rare unknown flanking DNA in highly complex samples, *Hum. Gene Ther.*, 12:743–749, 2001.
Triglia et al, A procedure for *in vitro* amplification of DNA segments that lie outside the boundaries of known sequences, *Nucleic Acids Res.*, 16:8186, 1988.
Rorth et al., Systematic gain–of–function genetics in Drosophilia, *Development*, 125:1049–1057, 1998.

* cited by examiner

*Primary Examiner*—Kenneth R. Horlick
*Assistant Examiner*—Heather G. Calamita
(74) *Attorney, Agent, or Firm*—Ingrid A. Beattie; Muntz, Levin, Cohn, Ferris, Glovsky and Popeo, P.C.

(57) ABSTRACT

The invention features a method for accelerating direct genome walking, which does not rely on restriction enzymes or ligases, and are therefore unaffected by the availability of useful restriction sites in the flanking region. The method is used to sequence genome segments that have previously been regarded unclonable and unsequenceable by the traditional methods.

4 Claims, 6 Drawing Sheets

```
                                                            1
cccgttatagcctttataagttaacaaaattaatgaataacgtaccagtcggtataaacc
ttggataattgttggattttatatgcagattcagcataaacatatttaggggaagaactt
                                         3
gtttattgttatggtgagatatgctgttttgctagtgtcagcacgtggcctgacaatcg
                2        N10
cctgccggaagcgtttaccggaaagttaagttttcagtttgattttgattgtactaaaga
gcgtatagctcacaaaactaactccagcttacgctgatattattgaattggttatcaagt
                                    4
cgtaagggttatttagaaacgctaagctcaaacaaacagttggtcagcgatccacccgga
                       5
gaagaaaatcaaagtcaatcccagactttactggaatcaggacaagtacgtggcatggat
acaatctcccacctacgccttttaattgttcaaggatacattacttatactgagaataga
gaatactgagtactnnnnnnnnnnnnnnnnnnnnnnnnnnnnnnnnnnnnnnnnnnnnnn
nnnnnnnnnnnnnnnnnnnnn...................nnnnnnnnnnnnnnnnnnn
cttgaatccaagagaaacacaaagcttttctcttcatgatcaaaaccctaaagtctaaa
gtccatattagaaaagctcgatacccgaggcttgaacgccaatcaaatcaggataattat
cagacttcagtttcagacctaattgtaaaaggtcggtgttcttctcaaataaaaagtttt
gtaatcatttagagaaataaaaattatatttttttcacttataaatattgcaagcattta
attttatatatgtaagacacgataagattgtaaacaaagctaatgaaaatgtataagag
                       6
gcggaatgcgagatgaaggatgcaggattcatcaccgcgatattcgaaccaaaggctggg
tacatcgcgatatttaatggagatatcgtgaaactacaaacagattgcggaccggagaag
```
SEQ ID NO 17.

Fig. 3A

LENGTH (UFW) : 509nt
LENGTH (PCR) : 509nt

1   UFW   aggatacattacttatactgagaatagagaatactgagtactGATACTAAAAAGCTAGGC
1   PCR   aggatacattacttatactgagaatagagaatactgagtactGATACTAAAAAGCTAGGC 61  UFW   GGAAATTCCGGTACCGACAGCGCCCCAGAAAAAACACTTATTTTTTTTAAAAAGACCAAC
61  PCR   GGAAATTCCGGTACCGACAGCGCCCCAGAAAAAACACTTATTTTTTTTAAAAAGACCAAC 121 UFW   AAGAATCAAAATACCTATTCATGGCGCAAAACAGTACAACAGTACTTACGAAGCTGTAAA
121 PCR   AAGAATCAAAATACCTATTCATGGCGCAAAACAGTACAACAGTACTTACGAAGCTGTAAA 181 UFW   CATGTCCCTAAAAGACAAAACTTTTCTGAGAGAATGTCTGGCCAAACGCGCCAGACAATG
181 PCR   CATGTCCCTAAAAGACAAAACTTTTCTGAGAGAATGTCTGGCCAAACGCGCCAGACAATG 241 UFW   TTTGAGCAAGCCCGCCAATGCGGAAGAAGATGAAGATTGTGAAAACGCAGTCGCTTTTAA
241 PCR   TTTGAGCAAGCCCGCCAATGCGGAAGAAGATGAAGATTGTGAAAACGCAGTCGCTTTTAA 301 UFW   TACGATTAAAGACGACAGTGACTCACTTGACTCCGACGACTTTATTAATTTTTTAGAGAA
301 PCR   TACGATTAAAGACGACAGTGACTCACTTGACTCCGACGACTTTATTAATTTTTTAGAGAA 361 UFW   AGGTCCCACTTGCCCATCGTTAACGAAGGCTGGCGGGAAGAACTATAAAAATCCCTATTG
361 PCR   AGGTCCCACTTGCCCATCGTTAACGAAGGCTGGCGGGAAGAACTATAAAAATCCCTATTG 421 UFW   ATACCGGAGCGGCATAAAATAATACAAAGCCCATAAAGGAGCTTGTCGACTACCCGTTCA
421 PCR   ATACCGGAGCGGCATAAAATAATACAAAGCCCATAAAGGAGCTTGTCGACTACCCGTTCA 481 UFW   CTGTGAGTTCCATCCATGTCTCCTATAAA  SEQ ID NO 18.
481 PCR   CTGTGAGTTCCATCCATGTCTCCTATAAA  SEQ ID NO 19.

Fig. 3C

SEQUENCE LISTING

<160> NUMBER OF SEQ ID NOS: 19

<210> SEQ ID NO 1
<211> LENGTH: 24
<212> TYPE: DNA
<213> ORGANISM: Artificial Sequence
<220> FEATURE:
<223> OTHER INFORMATION: Description of Artificial
      Sequence:oligonucleotide primer

<400> SEQUENCE: 1
cgaaatcatt aattgtggct tccg                                    24

<210> SEQ ID NO 2
<211> LENGTH: 30
<212> TYPE: DNA
<213> ORGANISM: Artificial Sequence
<220> FEATURE:
<223> OTHER INFORMATION: Description of Artificial
      Sequence:oligonucleotide primer
<220> FEATURE:
<221> NAME/KEY: misc_feature
<222> LOCATION: (21)..(30)
<223> OTHER INFORMATION: Wherein N is G or A or T or C

<400> SEQUENCE: 2
cttctcgtac atgctgcttc nnnnnnnnnn                              30

<210> SEQ ID NO 3
<211> LENGTH: 20
<212> TYPE: DNA
<213> ORGANISM: Artificial Sequence
<220> FEATURE:
<223> OTHER INFORMATION: Description of Artificial
      Sequence:oligonucleotide primer

<400> SEQUENCE: 3
gaatatgcag agcctcaacc                                         20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial
      Sequence:oligonucleotide primer

<400> SEQUENCE: 4
cgttcaccat tctactcgaa g                                       21

<210> SEQ ID NO 5
<211> LENGTH: 20
<212> TYPE: DNA
<213> ORGANISM: Artificial Sequence
<220> FEATURE:
<223> OTHER INFORMATION: Description of Artificial
      Sequence:oligonucleotide primer

<400> SEQUENCE: 5
tacatcattc gacccgaatg                                         20

<210> SEQ ID NO 6
<211> LENGTH: 523
<212> TYPE: DNA
<213> ORGANISM: Drosophila melanogaster

```
<400> SEQUENCE: 6
tatattctgc gactgtcgat gtcctaaaag gtccatcgcc ttctccaagt ttttctacgt      60
catacccttg cgtgcttgtt tatcttaaca actttataag gtcctagaaa ttttcctttc     120
aactttaacc cagttccacc tgttgtaatc actagatgct gaattttctg ctcctcacaa     180
tacaacttaa atgcctgtgc agtgaacgca gtcagagata atccgtaaag gatttccaaa     240
attagtagcc tgacgctcta gacaacttac aacttcctct gctcctgtgc tacgggtggg     300
atacaaccat acaaatttag aaaaaccgtg aactataact gaaatgtggt tgtagcgctt     360
gctcgtcatc tccaatggcc caacatggtc aatgtgatac gtcatcaacg gtcaatctcc     420
cttttcaatc ggggtcaaga aatcttcttt ctcccagct ttcgaattaa atacaataca      480
ctccacacaa ctgtccacaa cacgagcaac cgtttcttta agt                      523

<210> SEQ ID NO 7
<211> LENGTH: 25
<212> TYPE: DNA
<213> ORGANISM: Artificial Sequence
<220> FEATURE:
<223> OTHER INFORMATION: Description of Artificial
      Sequence:oligonucleotide primer

<400> SEQUENCE: 7
gaattaattt tactccagtc acagc                                           25

<210> SEQ ID NO 8
<211> LENGTH: 30
<212> TYPE: DNA
<213> ORGANISM: Artificial Sequence
<220> FEATURE:
<223> OTHER INFORMATION: Description of Artificial
      Sequence:oligonucleotide primer
<220> FEATURE:
<221> NAME/KEY: misc_feature
<222> LOCATION: (21)..(30)
<223> OTHER INFORMATION: Wherein N is G or A or T or C

<400> SEQUENCE: 8
attccacgta agggttaatg nnnnnnnnnn                                      30

<210> SEQ ID NO 9
<211> LENGTH: 28
<212> TYPE: DNA
<213> ORGANISM: Artificial Sequence
<220> FEATURE:
<223> OTHER INFORMATION: Description of Artificial
      Sequence:oligonucleotide primer

<400> SEQUENCE: 9
ctttgcagca aaatttgcaa tatttcat                                        28

<210> SEQ ID NO 10
<211> LENGTH: 20
<212> TYPE: DNA
<213> ORGANISM: Artificial Sequence
<220> FEATURE:
<223> OTHER INFORMATION: Description of Artificial
      Sequence:oligonucleotide primer

<400> SEQUENCE: 10
cgcacacaac ctttcctctc                                                 20

<210> SEQ ID NO 11
<211> LENGTH: 20
```

```
<212> TYPE: DNA
<213> ORGANISM: Artificial Sequence
<220> FEATURE:
<223> OTHER INFORMATION: Description of Artificial
      Sequence:oligonucleotide primer

<400> SEQUENCE: 11
caacaagcaa acgtgcactg                                              20

<210> SEQ ID NO 12
<211> LENGTH: 21
<212> TYPE: DNA
<213> ORGANISM: Artificial Sequence
<220> FEATURE:
<223> OTHER INFORMATION: Description of Artificial
      Sequence:oligonucleotide primer

<400> SEQUENCE: 12
gagttaattc aaaccccacg g                                            21

<210> SEQ ID NO 13
<211> LENGTH: 29
<212> TYPE: DNA
<213> ORGANISM: Artificial Sequence
<220> FEATURE:
<223> OTHER INFORMATION: Description of Artificial
      Sequence:oligonucleotide primer
<220> FEATURE:
<221> NAME/KEY: misc_feature
<222> LOCATION: (20)..(29)
<223> OTHER INFORMATION: Wherein N is G or A or T or C

<400> SEQUENCE: 13
caacaatcat atcgctgtcn nnnnnnnn                                     29

<210> SEQ ID NO 14
<211> LENGTH: 20
<212> TYPE: DNA
<213> ORGANISM: Artificial Sequence
<220> FEATURE:
<223> OTHER INFORMATION: Description of Artificial
      Sequence:oligonucleotide primer

<400> SEQUENCE: 14
ggacatgcta agggttaatc                                              20

<210> SEQ ID NO 15
<211> LENGTH: 23
<212> TYPE: DNA
<213> ORGANISM: Artificial Sequence
<220> FEATURE:
<223> OTHER INFORMATION: Description of Artificial
      Sequence:oligonucleotide primer

<400> SEQUENCE: 15
ctcactcaga ctcaatacga cac                                          23

<210> SEQ ID NO 16
<211> LENGTH: 24
<212> TYPE: DNA
<213> ORGANISM: Artificial Sequence
<220> FEATURE:
<223> OTHER INFORMATION: Description of Artificial
      Sequence:oligonucleotide primer

<400> SEQUENCE: 16
cactcagaat actattcctt tcac                                         24
```

<210> SEQ ID NO 17
<211> LENGTH: 999
<212> TYPE: DNA
<213> ORGANISM: Drosophila melanogaster
<220> FEATURE:
<221> NAME/KEY: misc_feature
<222> LOCATION: (495)..(579)
<223> OTHER INFORMATION: Wherein N is G or A or T or C

<400> SEQUENCE: 17

| | | | | | |
|---|---|---|---|---|---|
| cccgttatag | cctttataag | ttaacaaaat | taatgaataa | cgtaccagtc | ggtataaacc | 60 |
| ttggataatt | gttggatttt | atatgcagat | tcagcataaa | catatttagg | ggaagaactt | 120 |
| gtttattgtt | atggtgagat | atgctgtttt | tgctagtgtc | agcacgtggc | ctgacaatcg | 180 |
| cctgccggaa | gcgtttaccg | gaaagttaag | ttttcagttt | gattttgatt | gtactaaaga | 240 |
| gcgtatagct | cacaaaacta | actccagctt | acgctgatat | tattgaattg | gttatcaagt | 300 |
| cgtaagggtt | atttagaaac | gctaagctca | aacaaagagt | tggtcagcga | tccacccgga | 360 |
| gaagaaaatc | aaagtcaatc | ccagacttta | ctggaatcag | gacaagtacg | tggcatggat | 420 |
| acaatctccc | acctacgcct | tttaattgtt | caaggataca | ttacttatac | tgagaataga | 480 |
| gaatactgag | tactnnnnnn | nnnnnnnnnn | nnnnnnnnnn | nnnnnnnnnn | nnnnnnnnnn | 540 |
| nnnnnnnnnn | nnnnnnnnnn | nnnnnnnnnn | nnnnnnnnnc | ttgaatccaa | gagaaacaca | 600 |
| aagcttttc | tcttcatgat | caaaacccta | agtctaaag | tccatattag | aaaagctcga | 660 |
| tacccgaggc | ttgaacgcca | atcaaatcag | gataattatc | agacttcagt | ttcagaccta | 720 |
| attgtaaaag | gtcggtgttc | ttctcaaata | aaaagttttg | taatcattta | gagaaataaa | 780 |
| aattatattt | ttttcactta | taaatattgc | aagcatttaa | ttttatatat | gtaagacacg | 840 |
| ataagattgt | aaacaaagct | aatgaaaaat | gtataagagg | cggaatgcga | gatgaaggat | 900 |
| gcaggattca | tcaccgcgat | attcgaacca | aaggctgggt | acatcgcgat | atttaatgga | 960 |
| gatatcgtga | aactacaaac | agattgcgga | ccggagaag | | | 999 |

<210> SEQ ID NO 18
<211> LENGTH: 509
<212> TYPE: DNA
<213> ORGANISM: Drosophila melanogaster

<400> SEQUENCE: 18

| | | | | | |
|---|---|---|---|---|---|
| aggatacatt | acttatactg | agaatagaga | atactgagta | ctgatactaa | aaagctaggc | 60 |
| ggaaattccg | gtaccgacag | cgccccagaa | aaaacactta | ttttttttaa | aaagaccaac | 120 |
| aagaatcaaa | atacctattc | atggcgcaaa | acagtacaac | agtacttacg | aagctgtaaa | 180 |
| catgtcccta | aaagacaaaa | cttttctgag | agaatgtctg | gccaaacgcg | ccagacaatg | 240 |
| tttgagcaag | cccgccaatg | cggaagaaga | tgaagattgt | gaaaacgcag | tcgcttttaa | 300 |
| tacgattaaa | gacgacagtg | actcacttga | ctccgacgac | tttattaatt | ttttagagaa | 360 |
| aggtccccact | tgcccatcgt | taacgaaggc | tggcgggaag | aactataaaa | atccctattg | 420 |
| ataccggagc | ggcataaaat | aatacaaagc | ccataaagga | gcttgtcgac | tacccgttca | 480 |
| ctgtgagttc | catccatgtc | tcctataaa | | | | 509 |

<210> SEQ ID NO 19
<211> LENGTH: 509
<212> TYPE: DNA
<213> ORGANISM: Drosophila melanogaster -continued

```
<400> SEQUENCE: 19
aggatacatt acttatactg agaatagaga atactgagta ctgatactaa aaagctaggc        60
ggaaattccg gtaccgacag cgccccagaa aaaacactta ttttttttaa aaagaccaac       120
aagaatcaaa atacctattc atggcgcaaa acagtacaac agtacttacg aagctgtaaa       180
catgtcccta aaagacaaaa cttttctgag agaatgtctg gccaaacgcg ccagacaatg       240
tttgagcaag cccgccaatg cggaagaaga tgaagattgt gaaaacgcag tcgcttttaa       300
tacgattaaa gacgacagtg actcacttga ctccgacgac tttattaatt ttttagagaa       360
aggtcccact tgcccatcgt taacgaaggc tggcgggaag aactataaaa atccctattg       420
ataccggagc ggcataaaat aatacaaagc ccataaagga gcttgtcgac tacccgttca       480
ctgtgagttc catccatgtc tcctataaa                                         509
```

METHOD FOR ACCELERATED GENOME WALKING AND DNA FINGERPRINTING

This application claims priority to provisional patent application U.S. Ser. No. 60/277,690 filed Mar. 21, 2001, the entire contents of which is hereby incorporated by reference.

BACKGROUND OF THE INVENTION

The invention relates to DNA amplification and analysis.

A variety of DNA amplification methods have been previously reported that deal with sequence analysis of an uncharacterized region adjacent to a known element. Those methods include inverse PCR (iPCR) [Ochman et. al., Genetics 120:621–623 (1988); Triglia et. al., Nucleic Acids Res. 16:8186 (1988)], panhandle PCR [Jones and Winistorfer, Nucleic Acids Res. 20:595–600 (1992); Jones and Winistorfer, Biotechniques 23:132–138 (1997)], cassette ligation-anchored PCR [Mueller and Wold, Science 246:780–786 (1989)], vectorette-PCR [Riley et. al., Nucleic Acids Res. 18:2887–2890 (1990)], novel-Alu-PCR [Puskas et. al., Nucleic Acids Res. 22:3251–3252 (1994)] and Thermal Asymmetric Interlaced PCR (TAIL-PCR) [Liu and Whittier, Genomics 25:673–681 (1995)]. Despite various degrees of success, a number of drawbacks reduce the accuracy and efficiency of each of these methods.

SUMMARY OF THE INVENTION

The invention features a direct genome walking method, which overcomes many of the drawbacks of earlier methods by avoiding the need for restriction enzymes and ligases. Molecular cloning, which is often required in other sequencing methods, is also avoided.

The method produces a template for nucleotide sequence determination of an unknown sequence of a target nucleic acid molecule and is carried out by (a) contacting in the presence of a nucleic acid polymerase the target nucleic acid molecule with a first primer, the first primer being complementary to a first known sequence of the target nucleic acid to synthesize a first strand; (b) removing the first primer; (c) contacting the target nucleic acid molecule with a second primer, the second primer being complementary to a second known sequence of the target molecule at the 5' end and being random at the 3' end of the primer; (d) removing the second primer; (e) converting the sequence of the first strand to form a first strand lariat; (f) extending the lariat to complete a lariat stem to generate a template molecule which is suitable for sequencing using standard methods such as Sanger methodology; and (g) generating an amplicon by polymerase amplification. The amplicon is sequenced using conventional methods to determine the nucleotide sequence of the target nucleic acid. An amplicon is an amplified PCR product. The amplicon includes a nucleic acid of previously unknown sequence flanked by known sequences of the target nucleic acid molecule. Removal or destruction of the first primer is accomplished by exonuclease I (exoI). Similarly, the second primer is removed by exoI. ExoI-mediated primer removal is coordinate or stepwise.

The template molecule is amplified to generate a plurality of copies. The nucleotide sequence of the template molecule is determined using standard sequencing methods. Alternatively, a nucleic acid fingerprint, e.g., a DNA fingerprint, is generated by detecting the template molecule(s), e.g., by standard electrophoresis and visualization methods. The unknown sequence domain of the target nucleic acid molecule often does not contain restriction sites commonly used in conventional cloning techniques, e.g., EcoI, SacI, KpnI, SmaI, BamHI, XbaI, SalI, PstI, SphI, and HindIII. The fingerprint spans a domain of the nucleic acid molecule which does not contain one or more restriction enzyme cleavage sites such as those listed above.

The method utilizes nested primers, which are complementary to known sequences of the target nucleic acid molecule. Accordingly, the method also includes a step of contacting the target nucleic acid molecule, with a third primer, the third primer being complementary to a third known sequence located between the first and the second known sequences with respect to the target nucleic acid molecule as well as a step of contacting the target nucleic acid molecule with a fourth primer, the fourth primer being complementary to a fourth known sequence located 3' to the second primer with respect to the target nucleic acid molecule. The target nucleic acid molecule is contacted with a fifth primer, which is complementary to a fifth known sequence of target nucleic acid molecule. The fifth known sequence is adjacent to the unknown sequence of the target nucleic acid molecule and is nested to the fourth known sequence. The final products of the method are sequenced using conventional DNA sequencing methods.

The second primer is a hybrid primer containing sequence corresponding to known target sequence as well as a segment with random sequence. For example, at least 10 nucleotides of the second primer are complementary to the second known sequence, and at least 2, 5, 8, 9, 10 and up to 15 nucleotides at the 3'end of the second primer are random.

The hybrid oligonucleotide primer is designed with approximately 10 random bases at its 3' end, and with a specific sequence tag of approximately 15–20 bases at its 5' end. Sequence conversion and self-primed extension of the lariat is catalyzed by the still-active starting polymerase. The sequence conversion step mediated by still-active starting polymerase circumvents the need for ligation, which was typically required in earlier methods.

The average length of the first strand, and thus the walking range of the method, is controlled by the polymerase extension time. The DNA amplification is adjusted to favor synthesis of short (e.g., 0.5 kb or under in length), medium (e.g., 0.5 kb to approximately 1.5 kb in length), long (e.g. 1.5 kb to approximately 10 kb in length), or very long products (e.g., over 10 kb in length) and is directed by a primer(s) the same as, sequentially related to, or nested to the primer for the first-strand synthesis. Unlike existing systems, the walk length potential is at least 35 kb, and up to 50 kb and 100 kb in length. Prior to the invention, such lengths had not been accurately and reliably achieved in methods in which only one end of the DNA sequence was known.

Amplification and sequencing primers are nested, or internal to the original ends of a lariat molecule. Any part or whole of the amplification-, tagged-, or first-strand-primer can be homopolymeric. The polymerase to be used in the method is a psychrophile, mesophile, or thermophile or other extremophile, or is a blend that is a combination thereof. The polymerases are further characterized in that they are partly or wholly proofreading enzymes. The polymerase components can also be partly or wholly reverse transcriptases.

The method overcomes several drawbacks of earlier genome walking protocols. Previous methods required the use of restriction enzymes, presence of convenient restriction enzyme cleavage sites in the target DNA and use of DNA ligase. The present method is distinguished from earlier methods in that the method is carried out in the absence of a restriction enzyme. The method is also carried out in the absence of a DNA ligase. The unknown sequence of a target nucleic acid need not contain a restriction enzyme cleavage site, and the method generates sequence information for unknown sequence ranging in size from 0.5–100 kilobases. Typical walk distances range from 0.8–1.5 kilobases, and using longer extension times, from 30–35 kilobases.

The range of walk distance exceeds that achieved using earlier methods, and the method described herein overcomes the following drawbacks associated with prior methods: i) low specificity; ii) a limited range in genome walking; iii) a requirement for molecular cloning; iv) a requirement for restriction enzymes; v) a dependence on a favorable restriction map in the region of interest; vi) a dependence on ligation efficiency; and vii) low throughput.

The method has several advantages over known methods. For example, the method is performed in a single-buffer system, and reagents are directly added to a single buffer mixture in a single vessel such as a test tube or well of a microtiter plate. Volumes are typically in the microliter-scale volumes, but may be scaled up proportionately without sacrificing efficiency or accuracy. The method is performed with reactions in multitube-, multiwell-, or microplate arrays, with miniaturization to submicroliter volumes, or with other spatial economizing. An automated or semi-automated system is used to direct the amplification reactions. The method is automated using a robotic workstation and a multi-well reaction chamber format.

The target nucleic acid is RNA, DNA, or cDNA. Thus, another advantage is that the method can utilize RNA as a working material. Earlier methods which require restriction enzyme digestion cannot utilize RNA because it is not cut by restriction endonucleases.

Also within the invention is a DNA fingerprint or reproducible fragment size pattern of template molecules generated by the method. The molecules visualized in the fingerprint are a result of sequence- or conformation-related polymerase pausing sites having been encountered in the synthesis of the first strand of the method described above. The DNA fingerprint is a result of preferential primer binding sites having occurred during the random, pseudo-random or partially specific primer-annealing to the first strand of the method. The invention also includes a DNA fingerprint as a result of any combination, in any proportion, of the pausing sites in the synthesis of, and preferential primer-annealing to, the first strand of the method.

The method permits walking along any nucleic acid molecule in which at least one end is known. The method is particularly suitable for analyzing transposon sequences and sequences flanking the insertion site of the transposon, e.g., the known region is a transposable element. The known element is a viral sequence or a transposable element. Alternatively, the known element is a pathogen, or a natural or constructed gene or chromosome.

One of the most significant aspects of the invention is that the method reliably generates data over stretches of DNA that are difficult to sequence or are unsequenceable by conventional methods.

Other features, objects, and advantages of the invention will be apparent from the description and from the claims.

BRIEF DESCRIPTION OF THE DRAWINGS

FIG. 3A is a diagram of sequence from GENBANK™ accession no. AE003078, with the location of primers indicated above their respective target sequences. An excerpt from a previous Drosophila genome project entry, GENBANK™ accession no. AE003078, is shown starting from 5' nucleotide 4651, and containing a sequencing gap. Nucleotides in the excerpt are unnumbered due to upward base-count uncertainty presented by the gap. UFW primers: oligonucleotides 1 through 5, numbered according the scheme in FIG. 1B. Direct PCR primers: oligonucleotides 4 and 6.

FIG. 3C is a diagram showing UFW-derived sequence extending into the original gap of the GENBANK™ entry. New sequence is denoted in uppercase characters. UFW and direct PCR amplicons yielded identical sequences. UFW-derived sequence extended into the original gap of the entry.

DETAILED DESCRIPTION

The invention represents a highly compact system for accelerating direct genome walking. The method is termed UFW. Unlike previous walking techniques, the methods do not rely on restriction enzymes or ligases, and are therefore unaffected by the availability of useful restriction sites in the flanking region. A complete circumvention of molecular cloning steps permits this method to be used for sequencing genome segments that have previously been regarded unclonable and unsequenceable by the traditional methods. In one example, the system utilizes just four direct reagent additions, in microliter-scale volumes, over the course of a 6-hour procedure. The walk range in this method is directly related to the capabilities of the associated polymerase blend, indicating that it can achieve in excess of 35 kilobases per reaction. It also produces a DNA fingerprint that is distinctive to the flanking sequence. Despite the complexity of banding patterns in these fingerprints, the reaction products were directly sequenceable.

The method reliably generates sequence data independent of favorable/unfavorable restriction maps of unknown sequences in a target DNA and eliminates the need for DNA ligations. The results are consistent and reliable, throughput is high, and the walk distances achieved far exceed those achieved by present methods. The method provides DNA fingerprints of variable flanking regions and makes possible sequencing through some loci which were previously regarded as unsequenceable. Because addition of reagents is accomplished by direct addition into a single buffer system, miniaturization and automation of the method is facilitated.

Figure 1A:
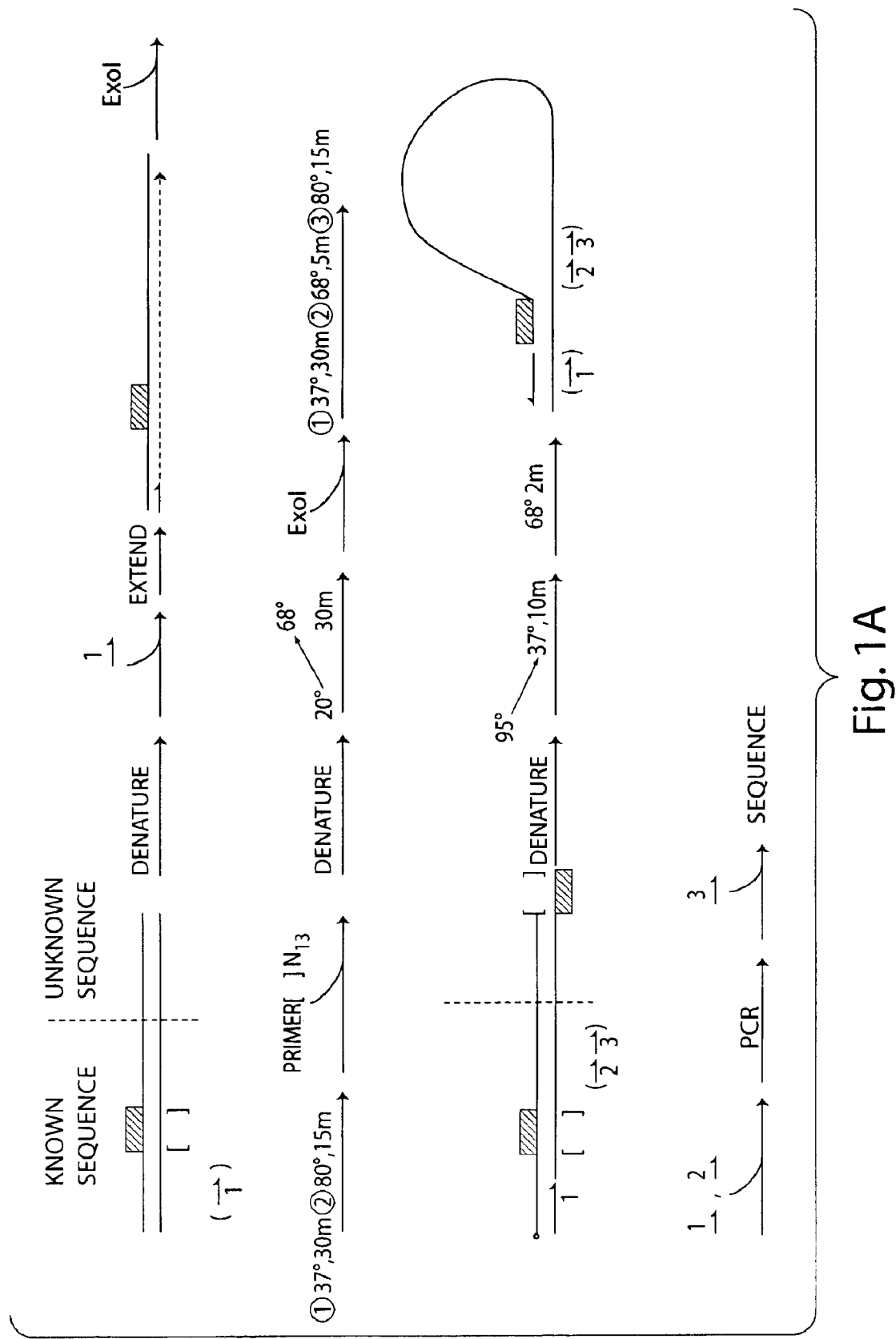
FIG. 1A is a diagram of the reactions of the UFW system.
Figure 1B:
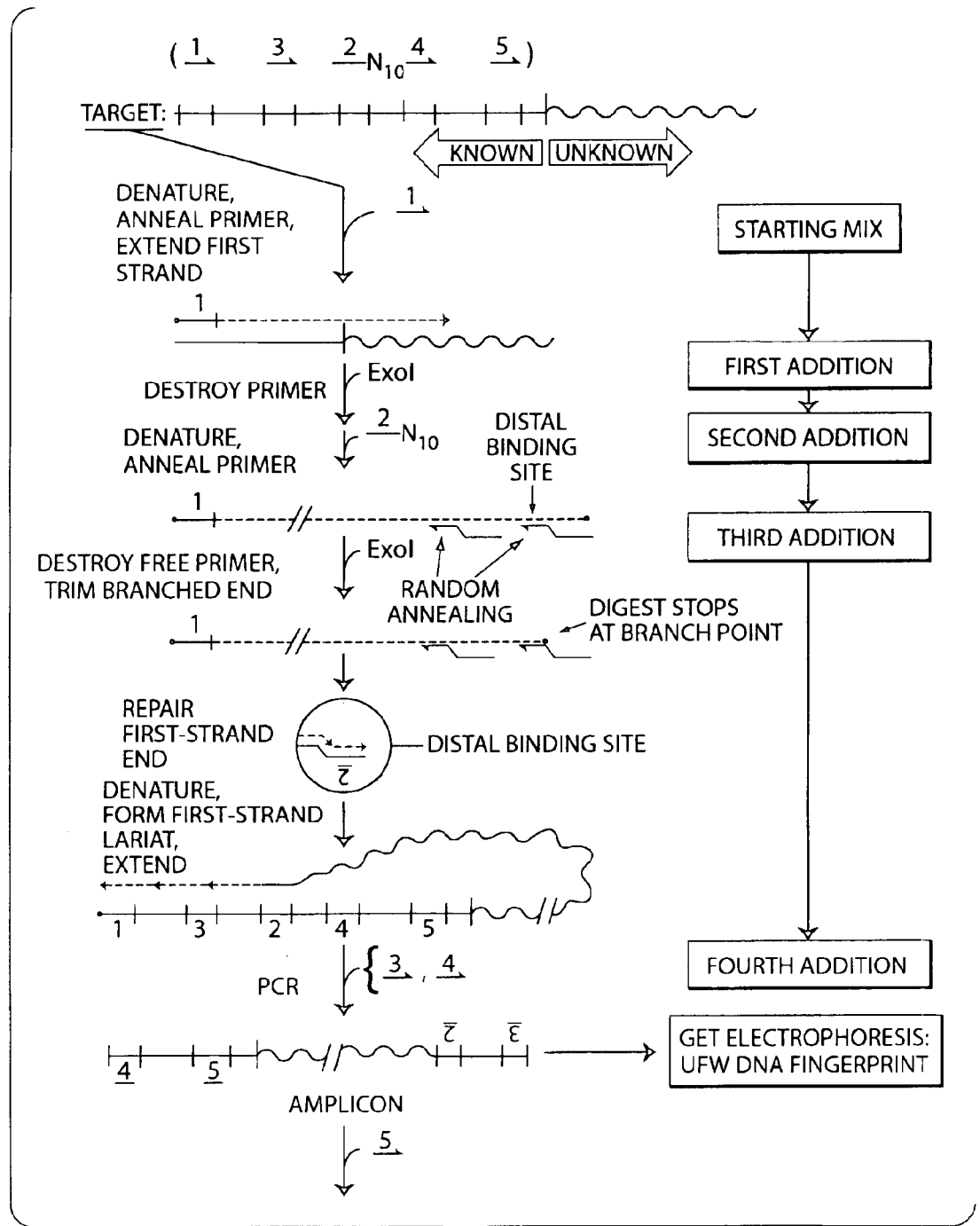
FIG. 1B is a diagram showing target DNA and primer configurations. Target DNA contains a known and an adjacent unknown (wavy line) sequence. The top line depicts the relative positions of UFW primers, which are numbered in the order of usage. Primers match the corresponding target sequences exactly, except that the primer 2 is appended by a 3' random 10-mer. Inverted numeric labels in the lower portion of the figure denote reversal of the original segment orientation.

The method is characterized by the following reactions: specific primer-directed extension into unknown flanking regions of DNA; destruction of free primer by exoI; annealing and short extension of sequence-tagged, random-ended primer opposite the first strand; exoI-directed removal of second primer and repair of branched ends; conversion of branched ends to a complement of the sequence tag; DNA denaturation and lariat formation by intramolecular annealing between the tag complement and a copy of the tag at the strand's other end; self-primed completion of the lariat; nested long and accurate polymerase chain reaction amplification (FIGS. 1A–B). The method yields a product suitable for conventional sequencing.

Figure 2:
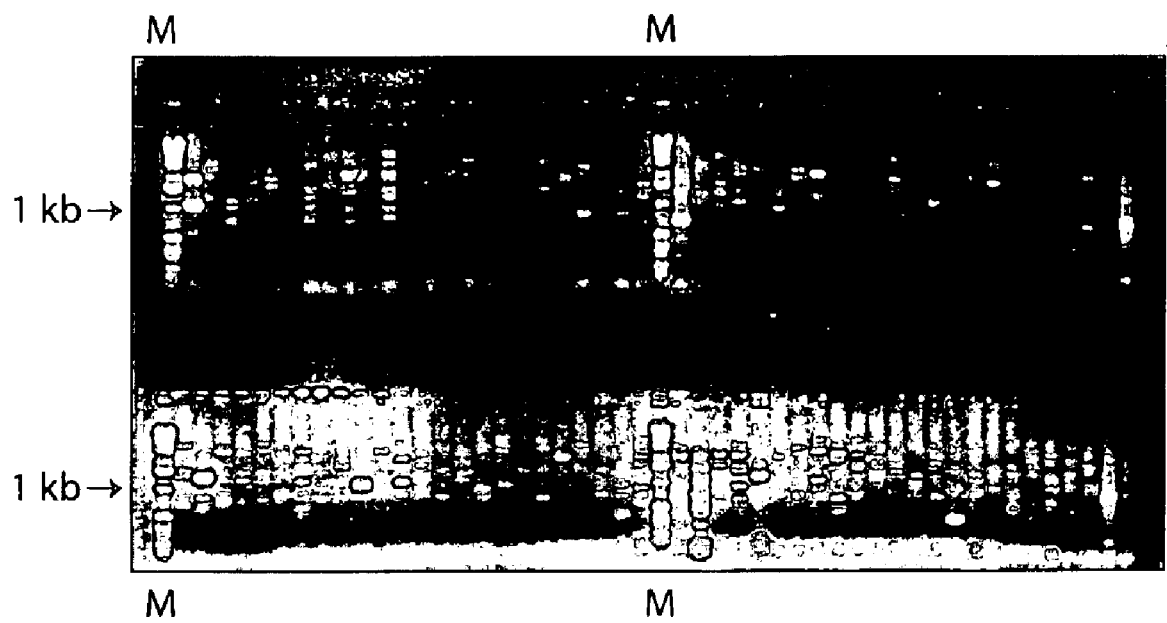
FIG. 2 is a photograph of an electrophoretic gel showing DNA fingerprints generated using the LFW system on 96 different short walks from P-element insertion sites in the Drosophila genome. The banding pattern in each lane is distinctive to the particular walk. Reactions were performed in a single 96-well PCR tray from start to finish. Lanes M: 1 kb ladder markers.

For example, the method for amplifying or recovering an unknown nucleic acid sequence adjacent to a known nucleic acid sequence includes at least two of the following steps: (a) polymerase-catalyzed extension from a known region into an unknown region by a primer-directed synthesis of a first strand; (b) enzymatic destruction of the first primer, typically using the single-strand-specific enzyme exonucleaseI (exoI); (c) strand denaturation, and annealing and short extension of a sequence-tagged, random-ended primer across the first strand; (d) destruction of the second primer and repair of the branched ends in the intermediate products, such that both events are simultaneously achieved by reintroduction of an exonuclease, e.g., exoI, an enzyme which digests single-stranded DNA from the 3' end, causing removal of free primer and trimming of branched DNA back to the branchpoint; (e) polymerase-catalyzed sequence conversion of the repaired ends that results in a complement to the specific sequence tag; (f) strand denaturation and formation of a lariat or stem-loop or panhandle structure by intrastrand annealing between the tag complement and a copy of the tag at the other end of the strand; (g) self-primed extension of the lariat; and (h) polymerase amplification to generate specific final products. An example of a DNA fingerprint generated using the described method is shown in FIG. 2.

The average genome walk distance is regulated by adjustments to the polymerase extension time in the first strand synthesis, thereby avoiding the problem of restriction fragment length limitations, a disadvantage of previous methods. In the usual form of the present invention, the reactions sit in a thermal cycler, to which microliter-scale volumes are directly added over the course of a few steps, in a single-buffer system, and without the large volume dilution-reconcentration cycles that defeat high throughput in other methods. The method relies on the formation of a DNA lariat, or stem-loop, or panhandle molecule, which is polymerase amplified; by comparison with previous panhandle-PCR methods, the present method, by its elimination of restriction-ligation and by its expandable walk length and intensive spatial economy, significantly improves the range, speed, and versatility of direct genome walking technology. This method allows the sequencing of elements currently regarded unsequenceable due to unclonability. The method also produces a DNA fingerprint of the variable flanking region.

The first-strand synthesis, extending from a known region into an unknown region, is primed typically by a specific oligonucleotide. The choice of polymerase, or blend of polymerases is based on such factors as the type of template (DNA or RNA), the level of desired sequence fidelity, and the desired length of the genome walk. For a DNA starting template, the polymerase is most usually a thermophile, or a blend of thermophiles, often including a proofreading polymerase. Alternatively, the polymerase blend includes a mesophilic or thermophilic reverse transcriptase, to accommodate an mRNA as the starting material; since the resulting first strand is a DNA, the remaining steps in this method would be essentially unaltered.

After first strand synthesis, the first primer is removed by destruction with a single-strand-specific enzyme, typically exonucleaseI (exoI), directly added to the reaction. If the temperature of the first-strand synthesis portion of this method had been raised on account of a thermophilic polymerase, the temperature is now lowered on account of the mesophilic exoI. It is not necessary to inactivate or remove the polymerase component, since the polymerase does not interfere with exoI; similarly, the exonuclease that remains throughout the course of this method does not impair subsequent polymerase activity.

Strand denaturation, and simultaneous inactivation of exoI is achieved by re-elevating the temperature in the reaction, to which is added a sequence-tagged, random-ended primer that is allowed to anneal opposite the first strand. This oligonucleotide primer is designed with typically 10 random bases at its 3' end, and with a specific sequence tag of 15–20 bases at the 5' end.

Following a short extension of the primer, fresh exoI is added for the simultaneous destruction of the second primer and the repair of the branched ends in the intermediate products. Since the exoI is single-strand-specific, exonucleolytic digestion continues only to the branch point, which does not present the free 3' DNA end that exoI requires for activity. The sequence of the repaired ends is then converted to the complement of the aforestated sequence tag; this conversion is accomplished by the filling-in of the ends initiating from the aforestated branch point, and is catalyzed by the starting polymerase, which has continued to remain active. The strands are denatured and a lariat or stem-loop or panhandle structure is produced by intrastrand annealing between the tag complement and a copy of the tag at the other end of the strand. The lariat then self-primes its own completion, where the event is catalyzed usually by the starting polymerase.

The completed lariat is subjected to a polymerase amplification to generate specific final products. The primer from the first-strand synthesis step is sufficient for this DNA amplication, but it is preferable to direct the amplification with primers that are nested, or internal, to the ends of the lariat molecule, in the interest of greater specificity and yield.

The final products, or amplicons, are subjected to agarose gel electrophoresis. The gel pattern, or size pattern, yields a DNA fingerprint that is particular to a combination of the flanking region's polymerase pause sites and its preferential binding sites for the second primer of this method.

The amplicons are also suitable for standard sequencing, without requiring molecular cloning; it is therefore possible to directly genome walk over a substantial distance, such that the range of the walk in this method is limited only by the capability of the polymerase component that is selected. The high performance of long-distance polymerases indicates that the current range of the UFW approaches and may exceed 50 kilobases per walk.

EXAMPLE 1
Reagents and Reaction Conditions

UFW is performed in a thermal cycler, e.g., in one such as the Biometra (Göttingen, Germany) which allows programmed pauses, permits temperature ramping, and which accommodates 96-well plates, as the Corning #6551 Thermowell plate with the #6555 sealing mat (Corning, Inc., Corning, N.Y.).

Reagents are added in 5 µl increments, directly to the reaction volume, which begins at 30 ul for first-strand synthesis, and culminates in a 50 µl DNA amplification reaction. The polymerase blend is TaKaRa LA-Taq (PanVera, Madison, Wis.), exonucleaseI (exoI) is from USB (Cleveland, Ohio), and primers are synthesized by Life Technologies, Inc. (Rockville, Md.) or by Sigma-Genosys (The Woodlands, Tex.). Below, primer 1, which is typically 20 nucleotides (nt) long, directs first-strand synthesis, primer 2, which is typically 26–30 nt in length, is the random-ended, sequence-tagged oligonucleotide, and primers 3 and 4, also each usually 20 nt in length, are nested PCR primers. Further, below, "cold-start" refers to the practice of adding in the polymerases to a reaction plate kept well beneath their working temperature, and then returning the plate to the cycler after the block has reached the denaturation temperature.

In the configuration described herein, which is suitable for transposon mapping, the proposed method takes 5 hours to produce the final amplicons.

The following are combined at reduced temperature:
1 µl genomic DNA (50 ng)
3 µl 10× PCR buffer
4.8 µl 10 mM dNTP mix
0.6 µl 75 ng/µl primer 1
0.5 µl TaKaRa LA-Taq
20.1 µl dH₂O (deionized water)

The mix is cold-started, denatured at 95 deg (degrees Celsius) for 3 min; brought to 55 deg, 30 sec; then 68 deg, 15 sec; and is paused at 37 deg.

Then exoI is added as a mix of
0.5 µl exoI (5 units)
0.5 µl 10× PCR buffer
4 µl dH2O and the reaction mix proceeds for 30 min at 37 deg; then is paused at 4 deg,
followed by adding a mix of
1 µl (150 ng) primer 2
0.5 µl 10× PCR buffer
3.2 µl 10 mM dNTP mix
0.3 µl dH₂O The reaction is cold-started, denatured 94 deg, 5 min; then 18 deg, 1 sec; 68 deg, 1 sec at 0.02 deg/sec to allow temperature ramping; then is paused at 4 deg.

Fresh exoI is added as a mix of
1 µl exoI (10 u)
0.5 µl 10× PCR buffer
3.5 µl dH₂O and the reaction mix incubated at 37 deg, 45 min; 68 deg, 15 min; 80 deg, 15 min; 95 deg, 3 min; 60 deg, 1 sec; 43 deg, 1 sec at 0.03 deg/sec for ramping; 68 deg, 2 min; then is paused at 4 deg.

The DNA is amplified by adding in a mix of
1 µl (75 ng) primer 3
1 µl (75 ng) primer 4
0.5 µl 10× TaKaRa buffer
2.5 µl dH₂O The reaction is cold-started, denatured 95 deg, 2.5 min, and run for 36 cycles of 95 deg, 30 sec; 53 deg, 30 sec; 68 deg, 1.5 min, adding 2 sec/cycle. This is completed by a final extension at 68 deg, 7 min.

The resulting DNA fingerprint is visualized as a size pattern on a standard agarose gel, generally prepared at 1.5% agarose.

For characterization of the flanking region, amplicons are rapidly purified by Qiagen filtration (Qiagen, Inc., Valencia, Calif.); standard chain-terminator sequencing is performed with the appropriate primer from the previous DNA amplification, or with another oligonucleotide, primer 5, nested to that.

The data shown in FIG. 2 were generated from reactions run in a standard 96-well microtiter plate. P-element UFW Primers used to generate the data shown in FIG. 2 are shown below in Table 1.

TABLE 1

| 5'-transposon end | 3'-transposon end |
|---|---|
| P5-1: gaattaattttactccagtcacagc (SEQ ID NO: 7) | P3-1: gagttaattcaaaccccacgg (SEQ ID NO: 12) |
| P5-2: attccacgtaagggttaatgnnnnnnnnnn (SEQ ID NO: 8) | P3-2: caacaatcatatcgctgtcnnnnnnnnnn (SEQ ID NO: 13) |
| P5-3: ctttgcagcaaaatttgcaatatttcat (SEQ ID NO: 9) | P3-3: ggacatgctaagggttaatc (SEQ ID NO: 14) |
| P5-4: cgcacacaaccttcctctc (SEQ ID NO: 10) | P3-4: ctcactcagactcaatacgacac (SEQ ID NO: 15) |
| P5-5: caacaagcaaacgtgcactg (SEQ ID NO: 11) | P3-5: cactcagaatactattcctttcac (SEQ ID NO: 16) |

Each primer sequence is shown 5'-to-3', and is named in the order of usage within UFW. These data demonstrate the high throughput capabilities of the UFW method.

EXAMPLE 2
Sequence Determination I

The methods described above were used to generate sequence data, i.e., walk, across a region of DNA that was unsequenceable by other methods. DNA is unsequenceable or difficult to sequence for a variety of reasons. Unsequenceable domains are frequently poor in restriction enzyme sites or contain heterochromatic DNA, which has few genes and many repeated regions that are difficult to maintain as clones for DNA sequencing. To demonstrate that the methods of the invention successfully walk across such previously unsequenceable DNA, an unfinished sequence, e.g., a DNA sequence with a gap in an unsequenceable area, was chosen. The DNA of GENBANK™ Accession No. AE003783 has a gap in its sequence, which may be due to any of the reasons for unsequenceability described above. The UFW method was used to generate sequence data which bridges the gap in the sequence. Table 2 shows the primers which were used in the method, and Table 3 shows the results of a genome walk in which new sequence (previously unknown DNA) was generated using UFW from one side (known DNA) of the gap in GENBANK™ Accession No. AE003783. Known sequence on one side of the gap is depicted in conventional typeface, and the new sequence generated using UFW is shown in bold type.

TABLE 2

Primers used in UFW Method

1: cgaaatcattaattgtggcttccg (SEQ ID NO: 1)
2: cttctcgtacatgctgcttcnnnnnnnnnnn (SEQ ID NO: 1)
3: gaatatgcagagcctcaacc (SEQ ID NO: 3)
4: cgttcaccattctactcgaag (SEQ ID NO: 4)
5: tacatcattcgacccgaatg (SEQ ID NO: 5)

TABLE 3

Determination of new sequence (in bold) by UFW in a gap area of GENBANK™ accession AE003783

(SEQ ID NO:6)
TATATTCTGCGACTGTCGATGTCCTAAAAGGTCCATCGCCTTCTCCAAG

TTTTTCTACGTCATACCCTTGCGTGCTTGTTTATCTTAACAACTTTATA

AGGTCCTAGAAATTTTCCTTTCAACTTTAACCCAGTTCCACCTGTTGTA

ATCACTAGATGCTGAATTTTCTGCTCCTCACAATACAACTTAAATGCCT

GTGCAGTGAACGCAGTCAGAGATAATCCGTAAAGGATTTCCAAAATTAG

TAGCCTGACGCTCTAGACAACTTACAACTTCCTCTGCTCCTGTGCTACG

GGTGGGATACAACCATACAAATTTAGAAAAACCGTGAACTATAACTGAA

ATGTGGTTGTAGCGCTTGCTCGTCATCTCCAATGGCCCAACATGGTCAA

TGTGATACGTCATCAACGGTCAATCTCCCTTTTCAATCGGGGTCAAGAA

ATCTTCTTTCTTCCCAGCTTTCGAATTAAATACAATACACTCCACACAA

CTGTCCACAACACGAGCAACCGTTTCTTTAAGT ...
(SEQ ID NO:6)

These data indicate that the methods described herein reliably and successfully walk across and generate sequence data in regions of DNA that have been difficult or impossible to sequence using other known methods.

EXAMPLE 3
Sequence Determination II

To further demonstrate the advantages of UFW, additional sequence for a second "unsequenceable" sample, Drosophila scaffold entry AE0003078 (originally submitted with an appreciable gap), was determined.

Genomic DNAs were isolated from Drosophila adults by a standard LiCl procedure, and custom oligonucleotides (FIG. 3A) were commercially obtained.

UFW was carried out as diagramatically depicted in FIGS. 1A–B. Specific reaction conditions are shown in Tables 1 and 2. The method included a 5–6 hour series of reactions, performed as a one-tube assay under a single thermal cycler program. The method included the following steps: a primer-directed first strand synthesis; destruction of the first primer with exonuclease I (exoI); strand denaturation and annealing of primer 2, which is random at its 3' end; a second exoI digest that simultaneously destroys free primer and trims the first strand back to its branch point with the bound, most distal, primer 2; sequence conversion at the 3' end of the first strand, by polymerase fill-in across the 5' (non-random) portion of primer 2; strand denaturation and first-strand lariat formation by intrastrand annealing between the tag complement, segment 2', and a copy of the tag, segment 2, near the other end of the strand; self-primed completion of the lariat stem; and PCR amplification, using the Takara long-and-accurate polymerase blend. Reactions were performed in the T-gradient Cycler (Biometra, Gottingen, Germany), an instrument capable of precision ramping control and programmed internal pauses.

For high throughput, additions of reagents throughout the procedure were made directly in 5 µl increments, up to a final reaction volume of 50 µl, such that the UFW reaction set was performed entirely within the same 96-well polypropylene PCR tray. The polymerase blend and exoI were both active in the PCR buffer supplied by the manufacturer, and were added sequentially to the reaction mix without cross-inhibition of one another. Specificity of amplification was promoted by full nesting of the PCR step using primers 3 and 4 (FIG. 1B), and by "cold-starting" (the practice of making additions well below the working temperature of the polymerase, then returning the PCR tray to the cycler after the unit has reached the denaturation temperature).

UFW products were analyzed by electrophoresis on 1.5% agarose gels. Amplicons were prepared for sequencing using standard reagents, e.g., QIAquick (Qiagen, Inc., Valencia, Calif.) or Montage (Millipore, Bedford, Mass.) PCR filtration units. DNA sequencing was carried out using standard nucleotide chain termination methods (Sanger et. al., 1977).

In developing a direct genome walking system, particular attention was paid to streamlining wherever possible to accelerate data acquisition. The methods were designed to bypass molecular cloning, and to abolish the restriction digests and ligations that are standard to prevailing methods such as inverse PCR (iPCR). A related benefit of these efficiencies is the removal of dilution-precipitation cycles, thereby realizing a strictly small-volume format. The method also maintains sufficient amplification specificity to allow direct sequencing without time-consuming agarose gel purification.

The straightforward procedure involves direct additions of microliter volumes into microliter volumes, within a standard 96-well tray from start to finish (Table 4).

TABLE 4

UFW: Standard Reaction Conditions

| Starting Mix | ExoI-digest I | Tagged-Random Priming | ExoI-digest II | Nested PCR |
| --- | --- | --- | --- | --- |
| 1 µl genomic DNA (50–100 ng) | Add a pre-mix of: | Add a pre-mix of: | Add a pre-mix of: | Add a pre-mix of: |
| 3 µl 10X PCR buffer | 0.5 µl exoI (5 units) | 1 µl (15 pmol) primer 2 | 1 µl exoI (10 units) | 1 µl (10 pmol) primer 3 |
| 4.8 µl 10 mM dNTP mix | 0.5 µl 10X PCR buffer | 0.5 µl 10X PCR buffer | 0.5 µl 10X PCR buffer | 1 µl (10 pmol) primer 4 |
| 0.6 µl (6 pmol) primer 1 | 4 µl dH$_2$O | 3.2 µl 10 mM dNTP mix | 3.5 µl dH$_2$O | 0.5 µl (10X PCR buffer |
| 0.5 µl Takara LA-Taq (2.5 units) | | 0.3 µl dH$_2$O | | 2.5 µl dH$_2$O |
| 20.1 µl dH$_2$O | | | | |

TABLE 4-continued

UFW: Standard Reaction Conditions

| Starting Mix | ExoI-digest I | Tagged-Random Priming | ExoI-digest II | Nested PCR |
|---|---|---|---|---|
| Cold-start, denature at 95°, 3 min; 51°, 30 sec; 68°, 15 sec; pause at 37° | 37°, 30 min; pause at 4° | Cold-start, denature 94°, 5 min; 18°, 1 sec; 68°, 1 sec at .02 degrees/sec for ramping; pause at 4° | 37°, 45 min; 68°, 15 min; 80°, 15 min; 95°, 3 min; 60°, 1 sec; 43°, 1 sec at .03 degrees/sec for ramping; 68°, 2 min; pause at 4° | Cold-start, denature 95°, 2.5 min, then run 36 cycles of: 95°, 30 sec; 51°, 30 sec; 68°, 1.5 min, adding 2 sec/cycle. A final extension is at 68°, 7 min |
| Comments: Specific primer-directed first-strand synthesis. Walk distance is controlled primarily by the polymerase extension time. Annealing temperature is adjustable for the particular primer. Long-distance polymerases are preferred for all walk-lengths, on account of yield and consistency. | Comments: First primer destruct. This and subsequent additions may be from pre-mixes, for high throughput. | Comments: Random binding of 5'-tagged primer. Cold-start eliminates the need to heat-inactivate exol of the previous step. | Comments: Second primer destruct simultaneous with first-strand trimming. Sequence conversion at the 3' end of the first strand. First-strand lariat formation by intrastrand annealing and extension. | Comments: Amplification- and first-strand extension times may be jointly increased for longer walks. Nesting removes lariat stem. Annealing temperature is adjustable for T$_m$'s Listed parameters are for high throughput insertional element mapping. |

In the most typical form of this method, first strand extension is 15 seconds, yielding 0.8–1.5 kilobase (kb) bands (FIG. 2). This size range is appropriate for most laboratory's mapping requirements. Much longer (35–50 kb) final products are obtained by coordinately increasing the first-strand and PCR extension times. The walking range of the method is directly related to the capabilities of the polymerase blend and PCR extension times.

Following primer destruction by the single-strand-specific enzyme (e.g., using exoI), sequence modification of the 3' ends of the first strands was accomplished without ligation, by essentially random annealing of primer 2, an oligonucleotide had having 10 random bases at its 3' end, but having a specific 5' sequence, based on a motif from the known end of the first strand (FIGS. 1B and 3A). A second addition of exoI removes free primer, and concurrently removes the 3' end of the first strand until digestion arrives at the point of contact with the primer bound nearest that end, and hence farthest from the walk origin. The resulting 5' overhang is then filled in by the still-active polymerase, thus converting the first-strand ends to a new sequence, and setting up lariat formation by intrastrand annealing (FIG. 1B). These termini modifications do not involve restriction cutting, making this technique independent of the neighboring restriction sites, an important advantage when working in genome regions poor in restriction sites. Since the method avoids restriction enzyme based cloning and molecular cloning altogether, the method is useful for evaluating genome segments that have been characterized as unclonable, and thus unsequenceable.

Figure 3B:
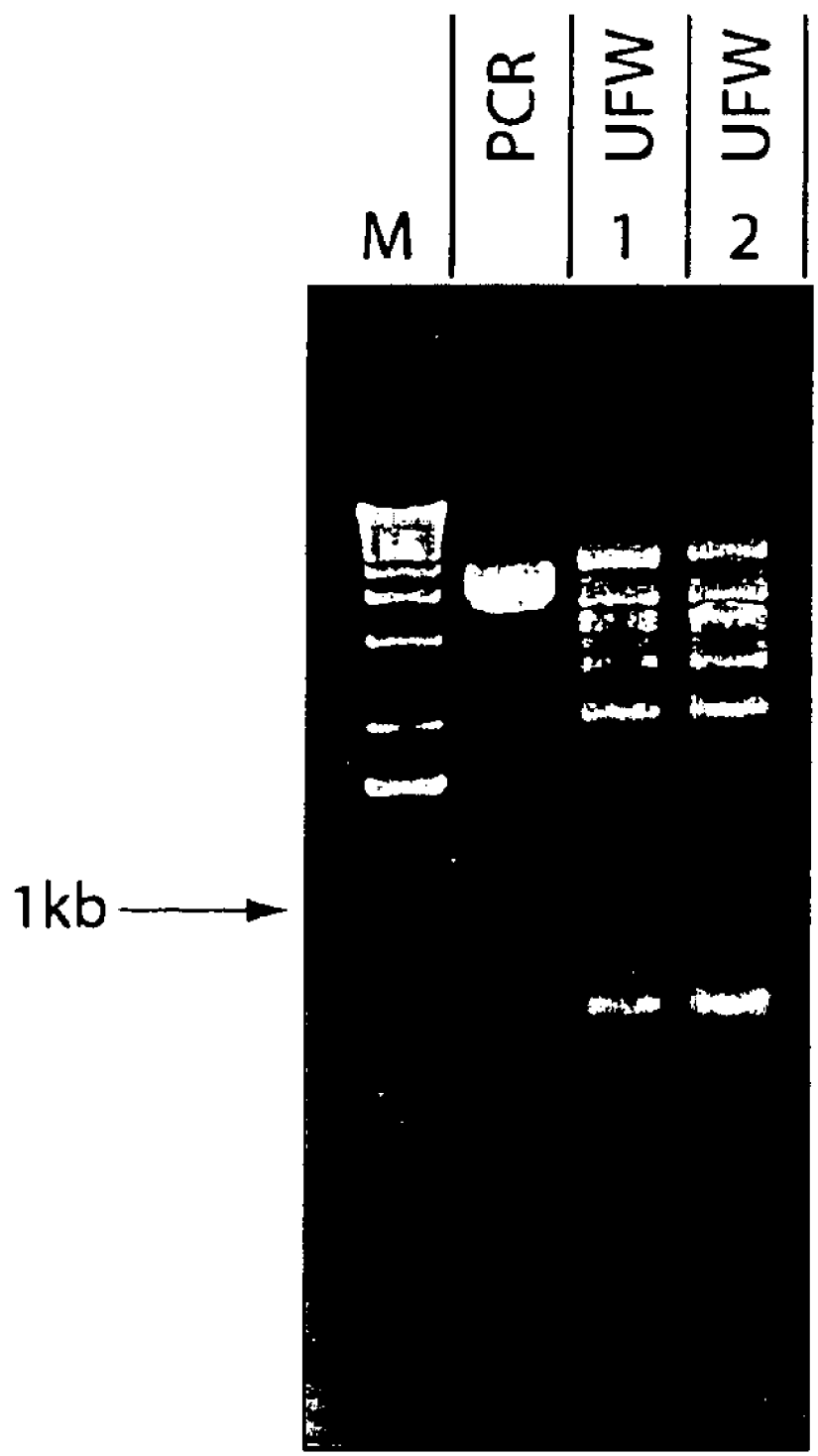
FIG. 3B is a photograph of an agarose gel showing PCR products spanning the sequencing gap in the originally-submitted sequence of AE003078. UFW and direct PCR products spanning the original sequencing gap are shown. Direct PCR was performed on 100 ng Drosophila genomic DNA, with the Takara LA-PCR polymerase blend. Primer annealing was at 60°, with an extension time of 5 minutes in each cycle. UFW results from two separate reactions document DNA fingerprint reproducibility. Lane M: 1 kb ladder markers.

FIGS. 3A–C show a determination of previously unknown sequence for a GENBANK™ entry, AE003078, which was originally submitted with an appreciable gap.

For primer selection in the final PCR step, a number of combinations generate amplicons—i.e., primers 1 and 3 individually or together, primers 1 and 4 together, or primers 3 and 4 together (FIG. 1B. However, the last primer pair, in addition to being fully nested, preferably favors removal of the lariat stem during amplification.

Banding patterns in agarose gels were somewhat complex, but consistently reproducible (FIG. 3B). The banding patterns generated by UFW represent a form of DNA fingerprinting that distinguishes between the different flanking regions (FIG. 2). This feature is best explained by a combination of a component of template site preferences in the annealing of primer 2, and polymerase pause sites (the polymerases used in this example, though thermophilic, are expected to be partially active during the 37 degree post-synthetic step). Here, it is important to note i) the specificity imparted by primer nestings at both the PCR and sequencing levels, and ii) the fact that the variously sized amplicons from a particular UFW reaction are related, and share a common terminus for sequence priming. Thus, despite the banding complexity, UFW molecules were reliably sequenced as directly as the standard specific PCR product, without specialized enrichments for the desired amplicon. UFW may be supplemented with the appropriate standard techniques, such as gel band extraction or molecular cloning of amplicons.

UFW is the most widely applicable approach for a first walk into any region when starting from a unique point of origin—and in principle, vis-a-vis competing, almost identical origins, a well-placed nucleotide difference, however small, in the first-strand primer design is likely to provide the specificity required of UFW. Further, since the maximum walk length is set by the most distal, not proximal, random binding site (FIG. 1B), UFW is truly "polymerase-driven". Advances in polymerase enzyme technology will yield data spanning ever longer intervals between the available UFW-accessible loci.

Besides direct genome walking, other uses of UFW include high throughput mapping of genome-wide insertional mutagenesis for functional genomics, identifying vector integration sites for gene therapy studies, and tracking of viral replication by detecting the insertional activity that accompanies productive infection, as with retroviruses. The manipulations for running UFW are conducive to automation.

UFW is useful for generating sequence information on unknown flanking sequence adjacent to known sequences. UFW is nonligational, eliminating concern over DNA ligase efficiencies. It is also nonrestrictional and free of molecular cloning, which lends the procedure to very high throughputs, and to the sequencing of previously unclonable/unsequenceable genome regions. The walking distance is not limited by the nature of the region's restriction map, but is a function of the polymerase, putting the present "reach" of this method at 50 kb per walk, given the performance of the currently available enzymes.

Other embodiments are within the following claims.

What is claimed is:

1. A method for producing a template for nucleotide sequence determination of an unknown sequence of a target nucleic acid molecule, comprising:
   (a) contacting in the presence of a nucleic acid polymerase said target nucleic acid molecule with a first primer, said first primer being complementary to a first known sequence of said target nucleic acid to synthesize a first strand;
   (b) removing said first primer;
   (c) contacting said target nucleic acid molecule with a second primer, said second primer being complementary to a second known sequence of said target molecule at the 5' end of said second primer and being random at the 3' end of said second primer;
   (d) removing said second primer;
   (e) trimming said first strand back to a branchpoint;
   (f) converting the sequence at said branchpoint of said first strand to form a first strand lariat;
   (g) extending said lariat to complete a lariat stem to generate a template molecule, said template molecule being suitable for sequence determination
wherein said method is carried out in the absence of a restriction enzyme.

2. A method for producing a template for nucleotide sequence determination of an unknown sequence of a target nucleic acid molecule, comprising:
   (a) contacting in the presence of a nucleic acid polymerase said target nucleic acid molecule with a first primer, said first primmer being complementary to a first known sequence of said target nucleic acid to synthesize a first strand;
   (b) removing said first primer;
   (c) contacting said target nucleic acid molecule with a second primer, said second primer being complementary to a second known sequence of said target molecule at the 5' end of said second primer and being random at the 3' end of said second primer;
   (d) removing said second primer;
   (e) trimming said first strand back to a branchpoint;
   (f) converting the sequence at said branchpoint of said first strand to form a first strand lariat;
   (g) extending said lariat to complete a lariat stem to generate a template molecule, said template molecule being suitable for sequence determination,
wherein said method is carried out in the absence of a DNA ligase.

3. A method for producing a template for nucleotide sequence determination of an unknown sequence of a target nucleic acid molecule; comprising:
   (a) contacting in the presence of a nucleic acid polymerase said target nucleic acid molecule with a first primer, said first primer being complementary to a first known sequence of said target nucleic acid to synthesize a first strand;
   (b) removing said first primer;
   (c) contacting said target nucleic acid molecule with a second primer, said second primer being complementary to a second known sequence of said target molecule at the 5' end of said second primer and being random at the 3' end of said second primer;
   (d) removing said second primer;
   (e) trimming said first strand back to a branchpoint;
   (f) converting the sequence at said branchpoint of said first strand to form a first strand lariat;
   (g) extending said lariat to complete a lariat stem to generate a template molecule, said template molecule being suitable for sequence determination,
wherein said unknown sequence does not comprise a restriction enzyme cleavage site.

4. The method of claim 3, wherein said unknown sequence does not comprise a restriction enzyme cleavage site selected from the group consisting of EcoR1, SacI, KpnI, SmaI, BamHI, XbaI, SalI, PstI, SphI, and HindIII.

* * * * *

UNITED STATES PATENT AND TRADEMARK OFFICE
CERTIFICATE OF CORRECTION

PATENT NO.    : 6,929,914 B2
DATED         : August 16, 2005
INVENTOR(S)   : Kyl V. Myrick It is certified that error appears in the above-identified patent and that said Letters Patent is hereby corrected as shown below:

Title page,
Insert -- STATEMENT AS TO FEDERALLY SPONSORED RESEARCH
    This invention was made with Government support under NIH Grant No. GM53249 and the Government therefore has certain rights in this invention. --.

Signed and Sealed this

First Day of November, 2005

JON W. DUDAS
*Director of the United States Patent and Trademark Office*